United States Patent
Murphy (10) Patent No.: US 9,821,033 B2
(45) Date of Patent: Nov. 21, 2017

(54) MODULATING BONE GROWTH IN TREATING SCOLIOSIS

(75) Inventor: Kieran Murphy, Toronto (CA)

(73) Assignee: KIERAN MURPHY LLC, Towson, MD (US)

( * ) Notice: Subject to any disclaimer, the term of this patent is extended or adjusted under 35 U.S.C. 154(b) by 1287 days.

(21) Appl. No.: 12/713,305

(22) Filed: Feb. 26, 2010

(65) Prior Publication Data

US 2010/0221229 A1     Sep. 2, 2010

Related U.S. Application Data

(60) Provisional application No. 61/156,081, filed on Feb. 27, 2009.

(51) Int. Cl.

| A61K 38/27 | (2006.01) |
| A61K 31/00 | (2006.01) |
| A61K 31/427 | (2006.01) |
| A61K 31/704 | (2006.01) |
| A61K 35/545 | (2015.01) |
| A61K 38/18 | (2006.01) |
| A61K 38/22 | (2006.01) |

(52) U.S. Cl.
CPC .............. *A61K 38/27* (2013.01); *A61K 31/00* (2013.01); *A61K 31/427* (2013.01); *A61K 31/704* (2013.01); *A61K 35/545* (2013.01); *A61K 38/18* (2013.01); *A61K 38/1875* (2013.01); *A61K 38/2242* (2013.01)

(58) Field of Classification Search
None
See application file for complete search history.

(56) References Cited

U.S. PATENT DOCUMENTS

| 5,612,315 A * | 3/1997 | Pikal et al. .................. 514/11.3 |
| 2001/0043940 A1* | 11/2001 | Boyce et al. ................. 424/423 |
| 2009/0130019 A1* | 5/2009 | Tobinick ....................... 424/1.49 |

OTHER PUBLICATIONS

Definition of Epiphysial plate, accessed at: http://www.stedmansonline.com/content.aspx?id=mlrE1600001891&termtype=t, on Oct. 29, 2015.*

* cited by examiner

*Primary Examiner* — Soren Harward
*Assistant Examiner* — Paul D. Pyla
(74) *Attorney, Agent, or Firm* — Perry & Currier Inc.

(57) ABSTRACT

The present specification provides, amongst other things, a method of treating scoliosis comprising delivering a therapeutically acceptable amount of a growth modulator to an epiphyseal growth plate to correct or compensate for disproportionate growth.

18 Claims, 8 Drawing Sheets

Fig.12

# MODULATING BONE GROWTH IN TREATING SCOLIOSIS

PRIORITY CLAIM

The present specification claims priority from U.S. Provisional Patent Application 61/156,081 filed Feb. 27, 2009, the contents of which are incorporated herein by reference.

FIELD

The present invention pertains to the field of scoliosis, in particular to the treatment of scoliosis using growth modulators.

SUMMARY

According to a first aspect, provided is a method of treating scoliosis, comprising delivering a therapeutically acceptable amount of a growth modulator to an epiphyseal growth plate to correct or compensate for disproportionate growth.

According to a further aspect, provided is a composition comprising a therapeutically acceptable amount of a growth modulator and a physiologically acceptable carrier for administration to an epiphyseal growth plate.

According to another aspect, provided is a method of treating scoliosis, comprising the delivery of a growth modulator to a target region of an epiphyseal growth plate for altering the growth in said target region.

According to a further aspect, provided is a method of treating scoliosis, comprising delivering a therapeutically acceptable amount of a growth modulator to selected portions of an epiphyseal growth plate to correct or compensate for disproportionate growth.

FIGURES

Embodiments of the present application will now be described, by way of example only, with reference to the attached Figures, wherein.

DESCRIPTION

Figure 1A:
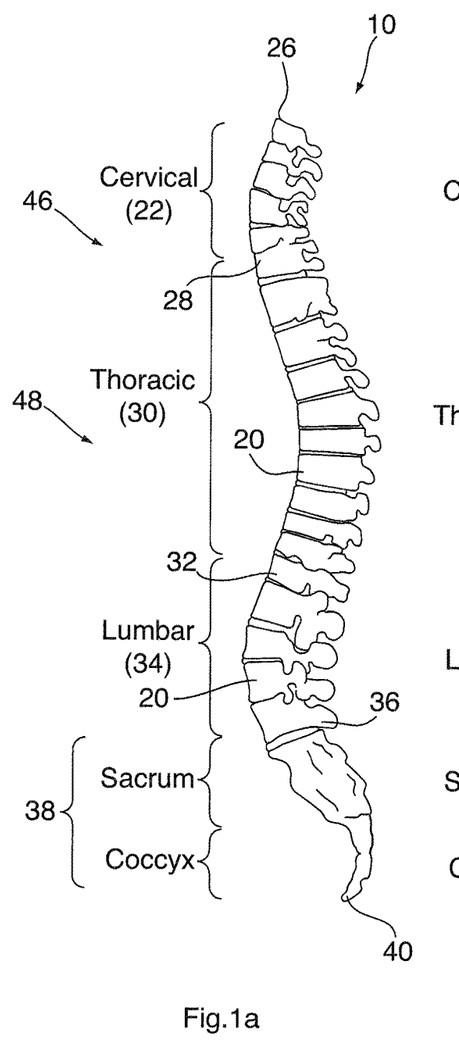
FIG. 1a is a lateral view of a healthy human vertebral column.
Figure 1B:
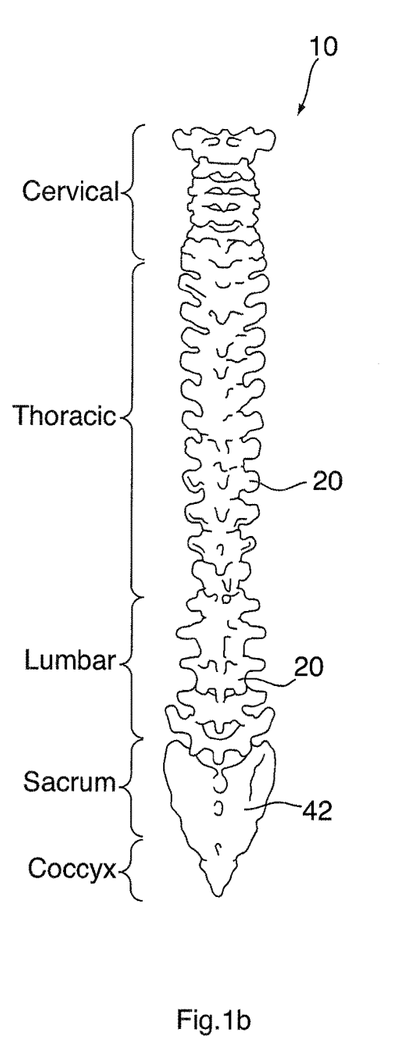
FIG. 1b is a posterior view of the healthy human vertebral column of FIG. 1.

Shown in FIG. 1a is a lateral view of a healthy human vertebral column 10. The vertebral column 10 is made up of 34 individual bony components termed vertebral bodies or vertebrae 20, and extends from the base of the skull to the pelvis. The vertebral column 10 is generally divided into 4 regions. The first region is called the cervical region 22, which begins at the apex of the odontoid process 26, and ends at the middle of the second thoracic vertebra 28. The second region is termed the thoracic region 30, and begins at the first thoracic vertebra 28 and ends at the middle of the twelfth thoracic vertebra 32. The third region is termed the lumbar region 34, and begins at the first lumbar vertebra 32, and ends at the sacrum 36. The fourth region is the pelvic region 38 (including the sacrum and coccyx), and begins at the first sacral vertebra articulation 36, and ends at the point of the sacro coccygeal junction 40. FIG. 1b presents the posterior view of the same healthy human vertebral column 10 shown in FIG. 1a.

The vertebrae 20 are generally regarded as the weight bearing structures of the vertebral column 10. The upper body weight is distributed through the vertebral column 10 to the sacrum 42 and pelvis (not shown). The curves of the vertebral column 10, namely the lordotic curve 46 (representative of the cervical region and lumbar region) and the kyphotic curve 48 (representative of the thoracic region), provide resistance and elasticity in distributing body weight and axial loads sustained during movement.

Figure 2:
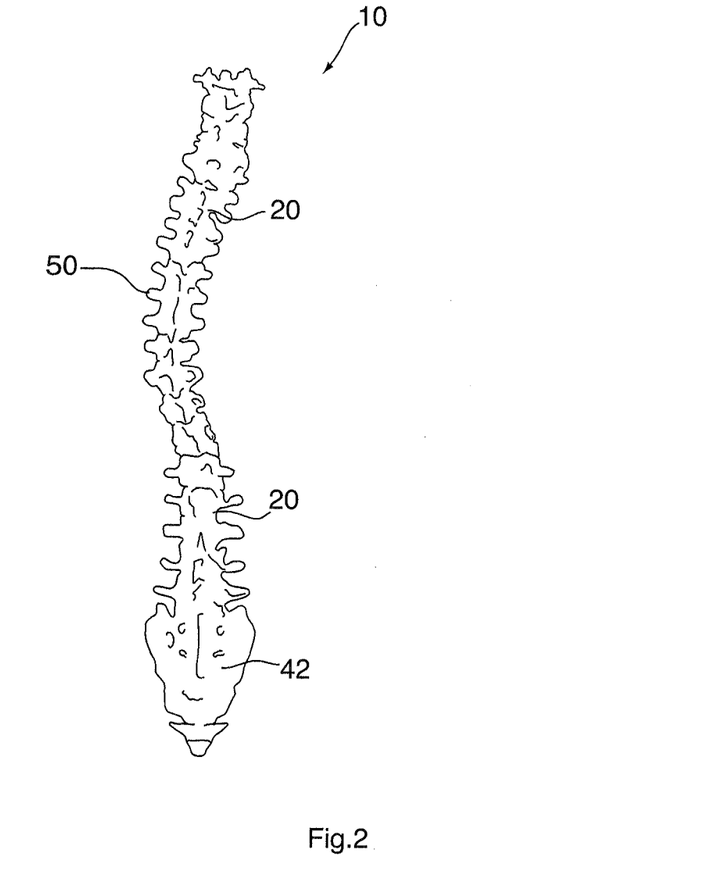
FIG. 2 is a posterior view of a scoliotic vertebral column.

Scoliosis is a condition in which the vertebral column 10 presents an abnormal lateral curvature, as shown in FIG. 2. Due to the imbalance caused by the lateral curvature 50, a potentially debilitating compression of one side of the body may result, often leaving the afflicted person with pain and reduced mobility usually proportional to the degree of the deformity. Scoliosis generally manifests during periods of growth, and is therefore most often noted in children and adolescents.

Figure 3:
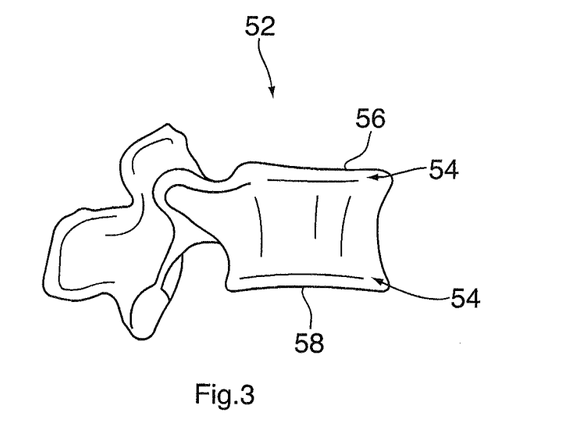
FIG. 3 is a side view of a typical vertebrae.

A typical adolescent vertebrae 52 is shown in isolation in FIG. 3. In a developing vertebrae, an epiphyseal growth plate 54 is located on each of the superior face 56 and inferior face 58 of the vertebrae 52. It is the epiphyseal growth plate 54 that is responsible for longitudinal growth of the vertebrae. Each epiphyseal growth plate 54 is generally made of hyaline cartilagenous tissue and comprises chondrocytes which are under constant division by mitosis. The chondrocytes stack facing the epiphysis (the end portion of the bone) while the older cells are pushed towards the diaphysis (the mid-section of the bone). As the older chondrocytes degenerate, osteoblasts ossify the remains to form new bone, a process known as ossification. Around the end of puberty, the epiphyseal cartilage cells stop duplicating and the entire cartilage is slowly replaced by bone, leaving only a thin epiphyseal line.

Figure 4A:
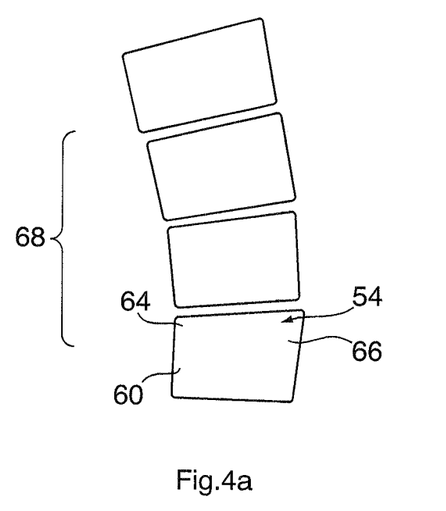
FIG. 4a is a schematic representation of a scoliotic vertebral column illustrating concavity in the defective region.
Figure 4B:
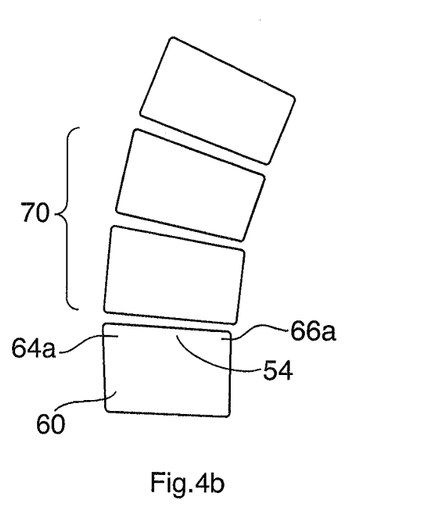
FIG. 4b is a schematic representation of a scoliotic vertebral column illustrating convexity in the defective region.

Disproportionate growth across the transverse plane of the epiphyseal growth plate 54 has the undesirable effect of introducing an irregular or wedge-type shape into the growing vertebrae, creating what is generally herein referred to as a defective vertebrae 60. For example, as shown in FIG. 4a, reduced activity on one side 64 of the epiphyseal growth plate 54 relative to the opposing side 66 manifests in the form of concavity 68 for that particular area. Similarly, increased activity on one side 64a relative to the opposing side 66a manifests in the form of convexity 70, as shown in FIG. 4b. Multiple zones of disproportionate growth can have serious implications for the afflicted individual, as evidenced by well documented cases of moderate to severe scoliosis.

In the various embodiments presented herein, disproportionate growth across the transverse plane of the epiphyseal growth plate 54 is treated through the introduction or application of at least one agent having the effect of modulating growth. For example, activity within the epiphyseal growth plate 54 can be modulated using suitable growth modulators (e.g. positive growth modulators to stimulate growth, negative growth modulators to inhibit growth). The introduction or application of growth modulators can be to either of, or both of the defective vertebrae 60 or an adjacent vertebrae 62, as explained more fully below.

As typically observed in congenital scoliosis, abnormal vertebrae growth arises from the premature partial fusion of the epiphyseal growth plate. In the region of premature partial fusion, the chondrocytes generally exhibit decreased activity, thereby retarding the growth of the defective vertebrae in the region of the partial fusion. The end effect is concavity in the region of partial fusion, as explained above having regard to FIG. 4a.

Figure 5A:
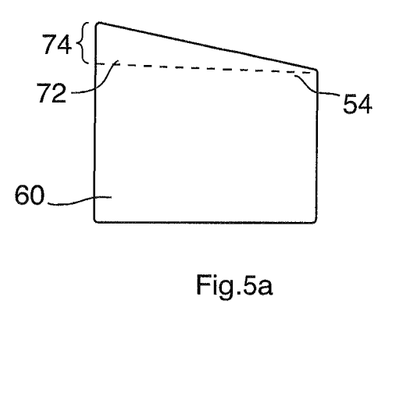
FIGS. 5a and 5b are a schematic representation of a treatment methodology using a negative growth modulator.
Figure 5B:
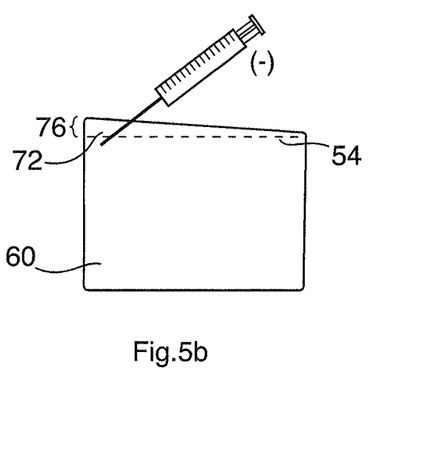

In one embodiment, shown schematically in FIGS. 5a and 5b, the disproportionate growth of the defective vertebrae 60 is modulated through the introduction or application of a suitable negative growth modulator into the region 72 of the epiphyseal growth plate 54 exhibiting normal growth function. By reducing growth function in the unfused sections of the epiphyseal growth plate 54, the extent of disproportionate growth is decreased, reducing the overall extent of wedge formation in the growing defective vertebrae 60. This approach to modulating growth is particularly useful when the manifestation of abnormal growth is caught early. As shown, FIG. 5a is intended to show the extent of disproportionate growth 74 in the untreated defective vertebrae 60 as compared to the limited disproportionate growth 76 in the treated defective vertebrae 60 shown in FIG. 5b.

Figure 6:
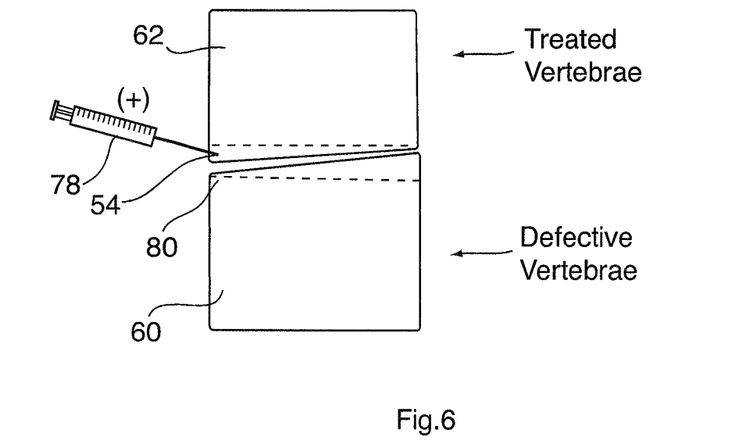
FIG. 6 is a schematic representation of a treatment methodology in which an adjacent vertebrae to a defective vertebrae receives a positive growth modulator.

Alternatively, as shown in FIG. 6, the disproportionate growth of a defective vertebrae 60 is addressed by modulating the growth of an adjacent vertebrae 62. In the scoliotic vertebral column, the growth of the vertebrae 62 adjacent to the defective vertebrae 60 can be stimulated in a manner that physiologically compensates for the disproportionate growth (e.g. angular defect) of the defective vertebrae 60. For example, a positive growth modulator 78 can be added into the epiphyseal growth plate 54 of the adjacent vertebrae 62, in the region immediately adjacent to the partially fused epiphyseal growth plate 80 of the defective vertebrae 60. As such, the adjacent vertebrae 62 demonstrates an induced disproportionate growth that effectively complements the angular defect of the defective vertebrae 60.

In other scoliotic conditions, such as some manifestations of idiopathic scoliosis, the disproportionate growth of a defective vertebrae may arise from the overactivity of certain zones of the epiphyseal growth plate. For example, disproportionate growth may be the result of normal growth activity on the concave side of the vertebral column, with concurrent overactivity on the convex side. In this situation, the overactivity can be addressed by introducing or applying a suitable negative growth modulator into the area demonstrating overactivity. Alternatively, a positive growth modulator may be introduced/applied to the area showing normal growth activity. As will be appreciated, negative and positive growth modulators can each be independently administered to separate zones of the same epiphyseal growth plate, as necessary to inhibit/promote growth during treatment.

In one embodiment for treating scoliosis, the first step involves a pre-operative survey and analysis of the defective vertebrae to identify the zones of the epiphyseal growth plate to which the growth modulator is to be introduced/applied. As such, the vertebral column is first imaged to provide the medical practitioner with an indication of the angular defects in the one or more defective vertebrae. A non-limiting example of suitable medical imaging methodologies that can be used to analyze the defective anatomy include x-ray, computerized tomography (CT), fluoroscopy, magnetic resonance imaging (MRI) and ultrasound. Based on the medical imaging, zones of increased/decreased growth activity are identified, allowing the medical practitioner to plan a suitable procedure of delivery of growth modulator to the appropriate zones of the epiphyseal growth plate.

The step of delivering the growth modulator is conducted under image guidance as generally known in the field of interventional radiology. In a non-limiting example, common interventional imaging methods include x-ray, CT, fluoroscopy, MRI and ultrasound.

Figure 7A:
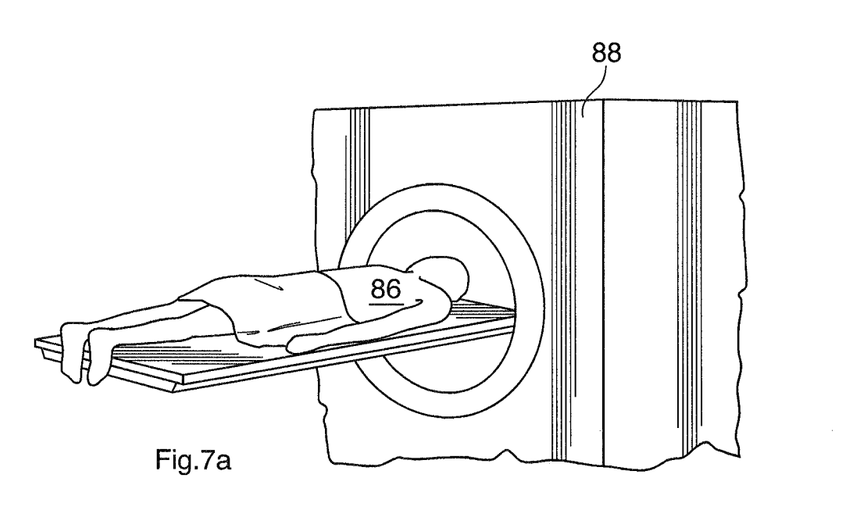
FIG. 7a shows a patient positioned for treatment relative to an imaging machine.
Figure 7B:
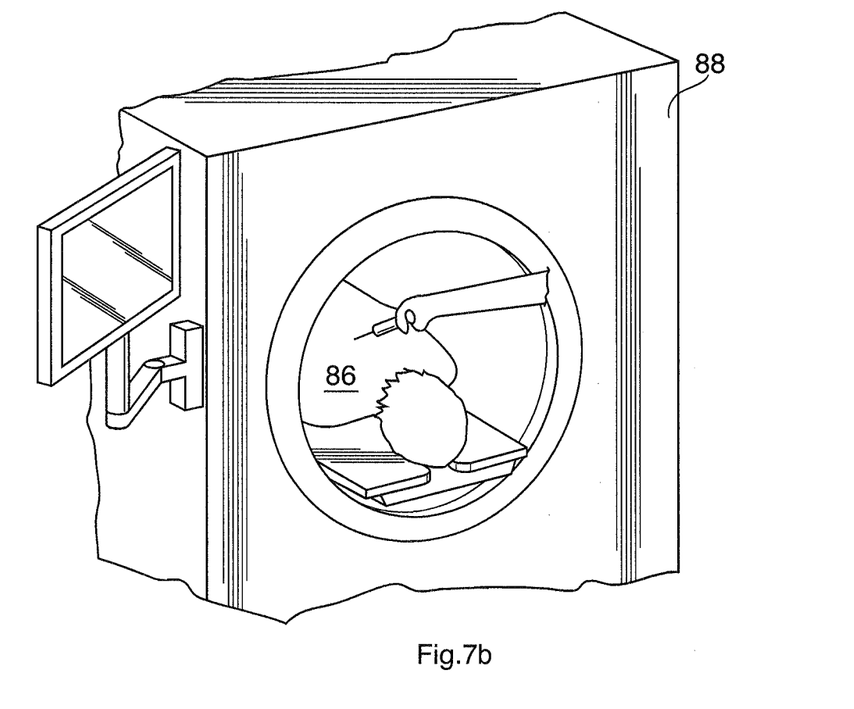
FIG. 7b shows a patent undergoing treatment during imaging.

For the purpose of explanation, the following description of one embodiment detailing an exemplary delivery procedure makes use of CT imaging for image guidance. It will be appreciated, however, that the procedure may be implemented using other suitable medical imaging technologies, such as the exemplary imaging technologies listed above. In this embodiment, as shown in FIG. 7a, a patient 86 is introduced into the CT scanner 88 and undergoes a pre-treatment diagnostic scan to identify the defective anatomy in the scoliotic vertebral column. The CT gantry is then suitably draped and readied, the skin is prepared and local anaesthetic is applied to the skin and adjacent soft tissue. As shown in FIG. 7b, the patient 86 is generally oriented face down to facilitate access to the vertebral column.

Figure 8:
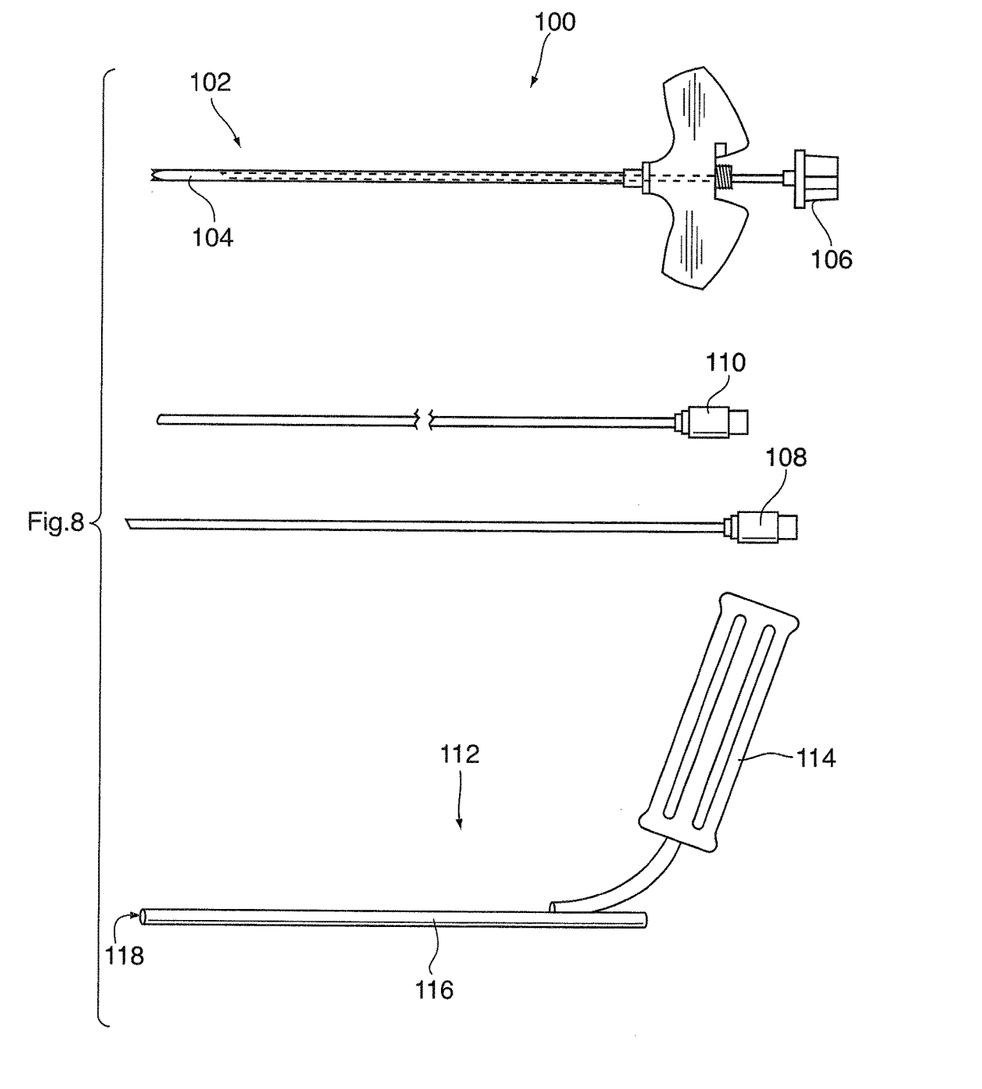
FIG. 8 is an exemplary kit of parts suitable for use in delivering the therapeutic agents to target bone.

As explained above, one or both of the inferior and superior epiphyseal growth plates may receive a growth modulator. The growth modulator is generally administered using a delivery device suitable for delivery of therapeutics into bone, such as a suitable needle for delivery of liquid or semi-liquid (e.g. semi-viscous liquid) formulations, or via a catheter device for delivery of solid and semi-solid formulations. Shown in FIG. 8 is an exemplary kit suitable for use in delivering the aforementioned therapeutics. In general, the kit 100 would include a piercing assembly 102 which comprises a hollow trocar 104 and a stylet 106 that is co-axially received through the hollow trocar 104. When the piercing assembly 102 is assembled, the distal end of the trocar 104 and the tip of the stylet 106 forms a contiguous tip for piercing through tissue and bone. The contiguous tip may take on any variety of configurations, such as a three-sided point, a round arrow-head, or any other suitable arrangement suitable for piercing the intended tissue. Once the piercing and positioning of the piercing assembly 102 into the target bone is complete, the stylet 106 is removed to present the hollow trocar 104 through which a catheter 108 or needle 110 can be inserted to deliver the therapeutic agent(s).

The kit may also contain a needle holder 112 for maintaining the piercing assembly in position during manipulation. Needle holder is typically made of a plastic or other radiolucent material that does not appear under CT image guidance (or under the imaging beam of the particular imaging machine being used). Holder 112 is comprised of a handle portion 114 and a channel portion 116. As shown, handle portion 114 is substantially cylindrical, but can be any desired shape and length, again depending on the preferences and/or needs of the procedure and/or surgeon. Channel portion 116 is also substantially cylindrical, but is further characterized by a hollow channel 118 through which the piercing assembly can be passed, and it is presently preferred the hollow channel 118 is of a slightly larger diameter than the piercing assembly 102 to securely hold the piercing assembly 102 within the channel portion 116.

A range of delivery methodologies and trajectories can be used, depending on the location off the target zone(s), including but not limited to transpedicular delivery, lateral and parapedicular delivery, transdiscal delivery and discal delivery.

Figure 9A:
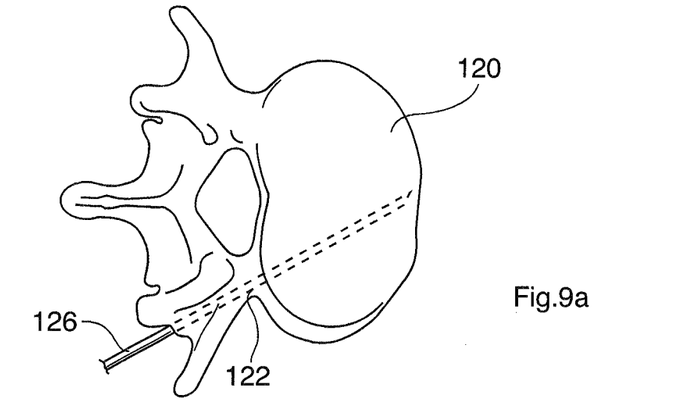
FIGS. 9a-9c show transpedicular delivery of the therapeutic agent.
Figure 9B:
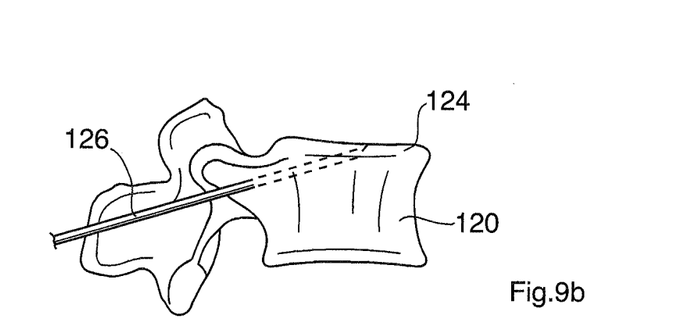
Figure 9C:
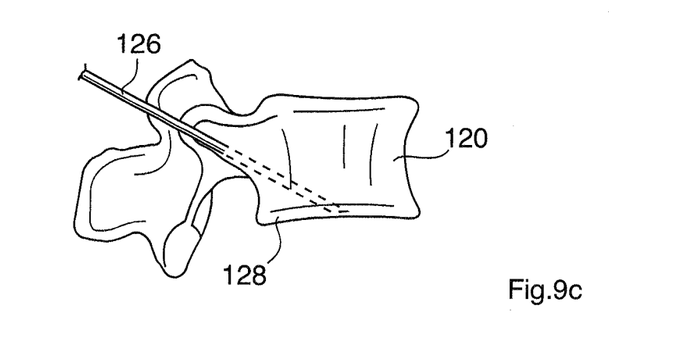

Shown in FIG. 9a is an example of transpedicular delivery wherein the growth modulator is delivered to the appropriate zone by penetrating the vertebrae 120 through the pedicle 122. For delivery to the superior epiphyseal growth plate 124, the delivery device 126 will generally penetrate the pedicle 122 at an angle as shown in FIG. 9b. Delivery to the inferior epiphyseal growth plate 128 will also generally require an angled penetration of the pedicle 122, as shown in FIG. 9c. As will be appreciated, the trajectory of the delivery device 126 will ultimately depend on the patients specific anatomy as well as any methodology preferences of the surgeon.

Figure 10:
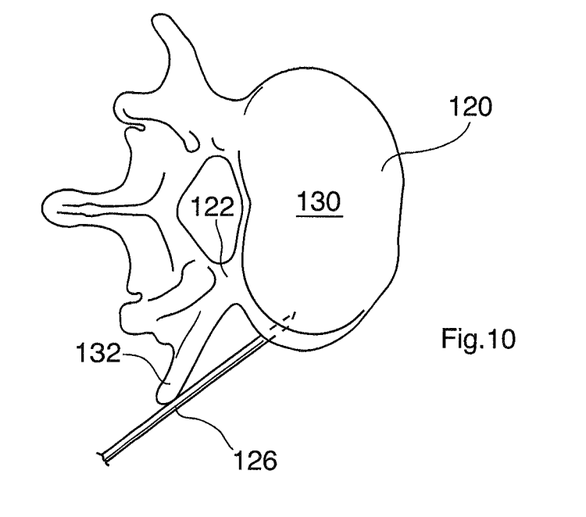
FIG. 10 shows parapedicular or lateral delivery of the therapeutic agent.

Alternatively, as shown in FIG. 10, the growth modulator may be delivered to the appropriate zone through parapedicular delivery wherein the delivery device 126 penetrates the body portion 130 of the vertebrae 120 without traversing the pedicle 122. For example, the delivery device 126 may have a trajectory that passes superior or inferior to the pedicle 122 and/or transverse process 132. Alternatively, the delivery device 126 may assume a trajectory that is generally anterior to the pedicle. While an angular trajectory into the body may be advantageous or preferred in certain circumstances, parapedicular delivery generally does not require an angular trajectory relative to the transverse plane of the vertebrae. With parapedicular delivery, the angle of delivery into the body of the vertebrae is generally decided upon by the medical practitioner as a matter of personal preference.

Figure 11:
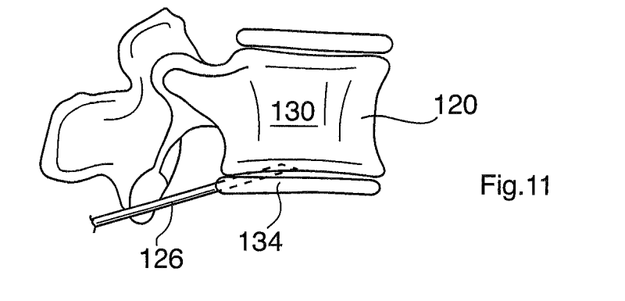
FIG. 11 shows transdiscal delivery of the therapeutic agent.

Transdiscal delivery, as shown in FIG. 11, is a further delivery option wherein the trajectory of the delivery device 126 results in a traversal of the adjacent intervertebral disk 134 into the body portion 130 of the vertebrae 120, in particular the target growth plate. As will be appreciated, transdiscal delivery is generally an angled trajectory relative to the transverse plane, as the target for delivery is the body of the vertebrae which lies either superior or inferior to the intervertebral disk 134.

Figure 12:
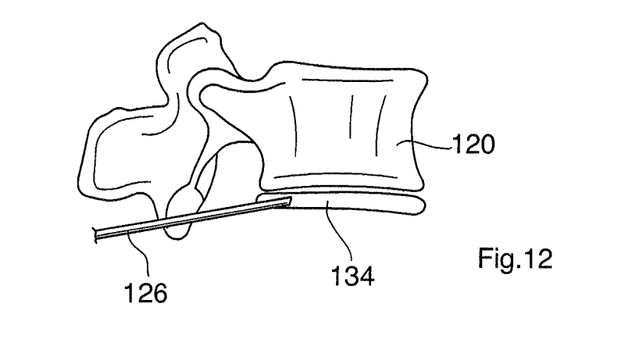
FIG. 12 shows discal delivery of the therapeutic agent.

The intervertebral disk 134 can also serve as a temporary reservoir of growth modulator. In this delivery methodology, termed discal delivery and shown in FIG. 12, the growth modulator is deposited within the fibrocartilaginous structure of the disk 134 wherefrom it diffuses into the adjacent vertebrae. To promote diffusion into the appropriate target area, the growth modulator is generally deposited into the disk in the area immediately adjacent to the area of the vertebrae 120 requiring growth modulation.

A number of positive growth modulators are contemplated for use. The following is intended as a non-limiting example of positive growth modulators that may be introduced into the epiphyseal growth plates to promote bone elongation. It will be appreciated that other positive growth modulators may be useful, as well as those that have yet to be developed, but ultimately find usage in promoting positive epiphyseal growth plate activity (e.g. bone elongation).

During natural bone elongation, the epiphyseal growth plates are responsive to the presence of growth hormone (GH). As such, natural growth hormone (e.g. somatotropin), biosynthetic (recombinant) human growth hormone, as well as suitable synthetic alternatives (e.g. exogenous bone growth stimulants, somatotropin analogues) may be used in accordance with the various embodiments described above. Exemplary recombinant growth hormones available include Nutropin (Genentech), Humatrope (Lilly), Genotropin (Pfizer), Norditropin (Novo), and Saizen (Merck Serono).

In addition to growth stimulants, a positive growth modulator may include a suitable inhibitor of endochondral ossification, the process of replacing cartilage with bone which generally occurs upon maturation and cessation of epiphyseal growth plate activity. For example, disproportionate growth across the transverse plane of a vertebrae can be induced by introducing an inhibitor of endochondral ossification. This methodology may be particularly useful in instances of adolescent scoliosis where ossification of the epiphyseal growth plates is beginning or about to occur. As the vertebrae approaches developmental maturity, the region receiving the endochondral ossification inhibitor will continue to grow, in comparison to the untreated zones of the epiphyseal growth plate. A non-limiting example of an agent that may be used to inhibit endochondral ossification includes chondromodulin-1.

Other suitable positive growth modulators that may find application include stem cells (e.g. mesenchymal stem cells (MSC)), chondrocyte growth factor (CGF), and natriuretic peptide (e.g. C-type natriuretic peptide).

Suitable negative growth modulators will include agents that cease chondrocyte proliferation/activity and/or promote ossification of the cartilagenous tissue. For example, agents that increase vascularization and promote the ossification of the epiphyseal growth plate tissue may be used. A non-limiting example of agents suitable for use as negative growth modulators include fibroblast growth factor (FGF), bone morphogenic proteins (BMPs), stem cells (e.g. mesenchymal stem cells (MSC)), vascular endothelial growth factor (VEGF), angiogenic growth factors, blood flow control agents and vascularity enhancing factors.

Other negative growth modulators will include chemotherapeutics, which generally interfere with the ability of cells to grow or multiply, and thus may find useful application in serving as a negative growth modulator. A non-limiting example of chemotherapeutic agents include alkylating agents (e.g. Cyclophosphamide, Mechlorethamine, Chlorambucil, Melphalan), anthracyclines (e.g. Daunorubicin, Doxorubicin, Epirubicin, Idarubicin, Mitoxantrone, Valrubicin), cytoskeletal disruptors (Paclitaxel, Docetaxel), epothilones, inhibitors of topoisomerase II (e.g. Etoposide, Teniposide, Tafluposide), nucleotide analogs and precursor analogs (e.g. Azacitidine, Azathioprine, Capecitabine, Cytarabine, Doxifluridine, Fluorouracil, Gemcitabine, Mercaptopurine, Methotrexate, Tioguanine), Peptide antibiotics (e.g. Bleomycin), platinum-based agents (e.g. Carboplatin, Cisplatin, Oxaliplatin), retinoids, and vinca alkaloids and derivatives (e.g. Vinblastine, Vincristine, Vindesine, Vinorelbine).

Additional agents that may act as negative growth modulators, some of which may also be classified as chemotherapeutics include antibiotics (e.g. tetracycline), antimitotics (e.g. methotrexate), antimicrobials, alcohols, proteins, disinfectants, hydroxyapatite, and metals (e.g. strontium).

Growth modulators that are delivered to the target area of the epiphyseal growth plate, or surrounding tissues may be present in the form of a pharmaceutical formulation. As such, the active agent, namely the growth modulator may be utilized together with one or more pharmaceutically acceptable carrier(s), and may optionally incorporate other therapeutic ingredients. The carrier(s) must be pharmaceutically acceptable in the sense of being compatible with the other ingredients of the formulation and not unduly deleterious to the recipient thereof. The active agent is provided in an amount effective to achieve the desired pharmacological effect, as described above.

To achieve the desired growth characteristics, the growth modulator may be directly injected into the target tissue. Alternatively, the growth modulator may be incorporated into pharmaceutically acceptable matrix suitable for depot into the target area. For example, the matrix can be formed into a pellet from which the growth modulator diffuses into the surrounding tissue. A non-limiting example of matrices useful for the delivery of the growth modulators include polymethylmethacrylate (PMMA) bone cement, biocompatible calcium phosphate-based formulations, and alginate polymers.

The aforementioned pharmaceutical formulation and/or matrix can also comprise a density eluting component that generally demonstrates elution characteristics proportional to the diffusion characteristics of the growth modulator. As the growth modulator dissipates into the tissue being treated, the density eluting agent (e.g. radio-opacifier) also dissipates, thereby resulting in a change in the associated Hounsfield density measurement of the tissue under treatment. As such, the amount of growth modulator in the tissue under treatment can be evaluated under a suitable imaging modality, for example CT. Following initial delivery into tissue under treatment, the medical practitioner can follow the dissipation of the growth modulator by monitoring the decrease in the Hounsfield density measurements, as evidenced by a decrease in image density of the tissue, as compared to baseline values established for untreated tissue. The return of the Hounsfield density measurements to pre-treatment levels is generally indicative of completed diffusion of the growth modulator into the tissue being treated. A non-limiting example of suitable materials for enhancing the Hounsfield density of the formulation include gold, iodine, ionic and non ionic iodinated compounds, ethiodol, and lipiodol, barium, tungsten, tantalum, gadolinium. Whatever material is chosen to enhance the Hounsfield density measurement, the amount and rate of dissolution of the radio-opacifying material is chosen to reduce toxicity experienced by the patient during dissolution.

The dose of the pharmaceutical composition may vary with the extent of growth modulation desired, the age of patient, and generally the extent of chondrogenesis/ossification in the target tissue. Typically, dosage regimes will be based on a dosage rate of 0.5-500 microgr/kg/day, but dosages greater than and less than this non-limiting example are contemplated.

The negative growth modulators may also be device-based, wherein disruption of chondrocyte activity, and more generally the growth noted in portions of the epiphyseal growth plate is accomplished through the use of ablation catheters. For example, catheters can be used to deliver one, or a combination of heat, and ultrasound to an area of tissue to be neutralized, for example to inhibit further growth of target areas of the epiphyseal growth plate. Ultrasound can be effectively used in radiofrequency ablation, in particular through the use of high intensity focused ultrasound (HIFU) or high energy interstitial ultrasound. The ablation catheter is directed to the region of interest using known techniques and apparatus, such as that used for the delivery of bone cement to a target region of bone. As will be appreciated, while ablation catheters are known, the catheters may be altered, for example with a curved tip to enhance contact with the endplates. Ablation catheters may be laser, radiofrequency ablation, high energy interstital ultrasound, or photonic, in nature. For example, a drug can be delivered systemically and distributed through out the body but only activated by direct exposure of light of certain wavelength through the action of a photonic catheter.

While generally described having regard to scoliosis, the use of growth modulators to modulate growth in vertebrae to compensate for disproportionate growth can also be used for other spinal curvature abnormalities. For example, disproportional grown across the transverse plane of the vertebrae either anterior or posterior to the frontal plane can result in kyphosis (abnormal backwards curvature) or Lordosis (abnormal forward curvature). Once again, where the abnormality is due to reduced and/or overactivity in the epiphyseal growth plate during development, the introduction of a suitable growth modulator can be used to arrest and/or physiologically compensate for the noted angular defect in the defective vertebrae.

The delivery/application of growth modulators into epiphyseal growth plates may also find application in the treatment of other bone formation abnormalities in which bone elongation can be used to correct for anatomical defects. For example, growth modulation in the epiphyseal growth plate may find application in the treatment of Genu valgum (commonly termed knock-knees), as well as in various dental and mandibular applications.

In addition to the foregoing, it is also contemplated to inject or deliver one or more of the foregoing drugs at the junction of the pedicle and the body of the vertebral body. Alternatively, or in addition to drugs, energy may be delivered, such as laser, photonic energy, cryo-ablation energy, or radio frequency energy or thermal energy towards achievement of one or more of the above effects.

It will be appreciated that, although embodiments have been described and illustrated in detail, various modifications and changes may be made. While several embodiments are described above, some of the features described above can be modified, replaced or even omitted. Further alternatives and modifications may occur to those skilled in the art. All such alternatives and modifications are believed to be within the scope of the invention and are covered by the claims appended hereto.

The invention claimed is:

1. A method of treating scoliosis, comprising injecting a therapeutically acceptable amount of a growth modulator into a first epiphyseal growth plate of a first vertebra for altering the growth of the first epiphyseal growth plate to correct or compensate for disproportionate growth.

2. The method of claim 1 wherein said growth modulator is a positive growth modulator to stimulate growth in the first epiphyseal growth plate.

3. The method of claim 2 wherein said first vertebra is a normal vertebra adjacent to a defective second vertebra exhibiting the disproportionate growth, such that stimulating the growth of the first epiphyseal growth plate physiologically compensates for the disproportionate growth of said defective second vertebra.

4. The method of claim 3 wherein a defective region of a second epiphyseal growth plate of said second vertebra is partially fused such that the disproportionate growth comprises insufficient growth in the defective region; the method comprising injecting the positive growth modulator to a target region of the first epiphyseal growth plate immediately adjacent to the defective region.

5. The method of claim 2 wherein said positive growth modulator comprises a natural growth hormone.

6. The method of claim 2 wherein said positive growth modulator comprises a biosynthetic human growth hormone.

7. The method of claim 2 wherein a positive growth modulator comprises an inhibitor of endochondral ossification.

8. The method of claim 7 wherein said inhibitor of endochondral ossification comprises chondromodulin-1.

9. The method of claim 2 wherein said positive growth modulator comprises one of stem cells, a chondrocyte growth factor (CGF), and a natriuretic peptide.

10. The method of claim 1 wherein said growth modulator is a negative growth modulator to inhibit growth.

11. The method of claim 3 wherein the negative growth modulator is introduced into an epiphyseal growth plate in order to decrease an extent of wedge formation in a growing defective vertebrae.

12. The method of claim 10 wherein said negative growth modulator comprises an agent that ceases chondrocyte activity or promotes ossification of the cartilagenous tissue.

13. The method of claim 10 wherein said negative growth modulator comprises agents that increase vascularization or promote the ossification of the epiphyseal growth plate tissue.

14. The method of claim 10 wherein said negative growth modulator comprises fibroblast growth factor (FGF), bone morphogenic proteins (BMPs), stem cells, vascular endothelial growth factor (VEGF), angiogenic growth factors, blood flow control agents and vascularity enhancing factors.

15. The method of claim 10 wherein said negative growth modulator comprises a chemotherapeutic agent therapeutically effective to interfere with an ability of cells to grow.

16. The method of claim 15 wherein said chemotherapeutic agent comprises one of alkylating agents, anthracyclines, cytoskeletal disruptors, epothilones, inhibitors of topoisomerase II, nucleotide analogs and precursor analogs, Peptide antibiotics, retinoids, and vinca alkaloids and derivatives.

17. The method of claim 10 wherein said negative growth modulator comprises one of an antibiotic, an antimitotic, an antimicrobial, an alcohol, a protein, a disinfectant, a hydroxyapatite, and a metal.

18. The method of claim 4, wherein injecting said therapeutically acceptable amount of said growth modulator to said target region produces a first angular defect in said first vertebra that is complementary to a second angular defect in said second vertebra.

* * * * *